US012339266B2

(12) United States Patent
Smith et al.

(10) Patent No.: US 12,339,266 B2
(45) Date of Patent: Jun. 24, 2025

(54) SUBTERRANEAN PARAMETER SENSING SYSTEMS AND METHODS

(71) Applicant: X Development LLC, Mountain View, CA (US)

(72) Inventors: Kevin Forsythe Smith, Pleasanton, CA (US); Artem Goncharuk, Mountain View, CA (US); Allen Richard Zhao, Mountain View, CA (US); Jonathan Gray Wilfong, San Carlos, CA (US)

(73) Assignee: X Development LLC, Mountain View, CA (US)

( * ) Notice: Subject to any disclaimer, the term of this patent is extended or adjusted under 35 U.S.C. 154(b) by 221 days.

(21) Appl. No.: 18/049,148

(22) Filed: Oct. 24, 2022

(65) Prior Publication Data

US 2023/0125404 A1 Apr. 27, 2023

Related U.S. Application Data

(60) Provisional application No. 63/270,951, filed on Oct. 22, 2021.

(51) Int. Cl.
*G01N 33/00* (2006.01)
*E21B 41/00* (2006.01)
(Continued)

(52) U.S. Cl.
CPC ....... *G01N 33/004* (2013.01); *E21B 41/0064* (2013.01); *E21B 47/117* (2020.05);
(Continued)

(58) Field of Classification Search
CPC .......... G01N 33/0036; G01N 33/0027; G01N 33/0009; G01N 33/004; G01V 1/16;
(Continued)

(56) References Cited

U.S. PATENT DOCUMENTS 10,260,316 B2   4/2019 Garcia et al.
2008/0115971 A1* 5/2008 Kelleher ............... E21B 21/001
                                                    175/40

(Continued)

FOREIGN PATENT DOCUMENTS

CN     115079250      9/2022
JP     2004219379 A  * 8/2004   ......... E21B 41/0064
WO   WO 2009/135172  11/2009

OTHER PUBLICATIONS

Abbott et al., "USArray: Geoscientists' "Earth Telescope"," Earth, Oct. 16, 2012, 57(11):40.

(Continued)

*Primary Examiner* — Benjamin R Schmitt
(74) *Attorney, Agent, or Firm* — Fish & Richardson P.C.

(57) ABSTRACT

A carbon dioxide ($CO_2$) sequestration sensor system includes an underground sub-assembly including one or more sensors configured to detect at least one attribute associated with $CO_2$ sequestration below a terranean surface; and an above-ground sub-assembly positionable on the terranean surface proximate the underground sub-assembly and including at least one controller communicably coupled to the one or more sensors.

32 Claims, 4 Drawing Sheets

(51) Int. Cl.
  *E21B 47/117* (2012.01)
  *E21B 47/12* (2012.01)
  *G01V 1/30* (2006.01)
  *G01V 1/18* (2006.01)

(52) U.S. Cl.
  CPC .............. *E21B 47/12* (2013.01); *G01V 1/306* (2013.01); *G01V 1/18* (2013.01); *Y02C 20/40* (2020.08)

(58) Field of Classification Search
  CPC . G01V 1/18; G01V 1/181; G01V 1/20; G01V 1/22; G01V 1/306; E21B 41/0064; E21B 47/00; E21B 47/117; E21B 47/12; G01P 15/00; Y02C 20/40
  See application file for complete search history.

(56) References Cited

U.S. PATENT DOCUMENTS

2013/0031955 A1* 2/2013 Zimbron ............ B01D 53/0415
  73/23.42
2017/0067843 A1* 3/2017 Rouchon ............... E21B 49/082
2018/0128084 A1* 5/2018 Garcia .................. E21B 47/117

OTHER PUBLICATIONS

International Search Report and Written Opinion in International Appln. No. PCT/US2022/047583, dated Jan. 20, 2023, 13 pages.

Schmidt-Hattenberger et al., "CO2 remove," Final Project Report Chapter 8—Ketzin Test Site, Jun. 30, 2012, 45 pages.

Tiwari et al., "4D Seismic in Subsurface CO2 Plume Monitoring—Why It matters?," Society of Petroleum Engineers, Sep. 21, 2021, 14 pages.

Tiwari et al., "IPTC-21213-MS Monitoring, Measurement and Verification MMV: A Critical Component in Making the CO2 Sequestration Success," International Petroleum Technology Conference, Apr. 32, 2021, 19 pages.

Zhan et al., "Distributed Acoustic Sensing Turns Fiber-Optic Cables into Sensitive Seismic Antennas," Seismological Research Letters, Dec. 4, 2019, 91(1):1-15.

Office Action in Australian Appln. No. 2022373526, mailed on Apr. 16, 2025, 3 pages.

* cited by examiner

SUBTERRANEAN PARAMETER SENSING SYSTEMS AND METHODS

CROSS-REFERENCE TO RELATED APPLICATION

This application claims priority under 35 U.S.C. § 119 to U.S. Provisional Patent Application Ser. No. 63/270,951, filed on Oct. 22, 2021, the entire contents of which are incorporated by reference herein.

TECHNICAL FIELD

This disclosure generally relates to subterranean parameter sensing systems and methods and, more particularly, carbon dioxide ($CO_2$) sequestration sensing systems and methods.

BACKGROUND

Carbon sequestration is the process of storing carbon in a carbon pool. In some aspects, the stored carbon can include $CO_2$. $CO_2$, for example that has been removed from the atmosphere, can also be stored in the Earth's crust by injecting it into the subsurface, or in the form of insoluble carbonate salts (mineral sequestration). These methods are considered non-volatile because they remove carbon from the atmosphere and sequester it indefinitely and presumably for a considerable duration (thousands to millions of years).

SUMMARY

In an example implementation, a $CO_2$ sequestration sensor system includes an underground sub-assembly including one or more sensors configured to detect at least one attribute associated with $CO_2$ sequestration below a terranean surface; and an above-ground sub-assembly positionable on the terranean surface proximate the underground sub-assembly and including at least one controller communicably coupled to the one or more sensors.

In an aspect combinable with the example implementation, the at least one attribute includes at least one of a $CO_2$ plume from below the terranean surface, a fracture generated by a $CO_2$ sequestration operation, or a change to a seismic condition below the terranean surface generated by the $CO_2$ sequestration operation.

In an aspect combinable with any one of the previous aspects, the one or more sensors include at least one of an accelerometer, a geophone, a $CO_2$ sensor, a DAS, an electromagnetic sensor, or a gravitometer.

In an aspect combinable with any one of the previous aspects, the underground sub-assembly further includes a conduit having at least one open end configured for insertion from the terranean surface into a subterranean zone to a particular depth, the conduit including a volume configured to at least partially enclose the one or more sensors.

In an aspect combinable with any one of the previous aspects, the particular depth is between 1-3 feet below the terranean surface.

In an aspect combinable with any one of the previous aspects, the conduit includes a hollow tube.

In an aspect combinable with any one of the previous aspects, the conduit includes a sharpened end configured to facilitate the insertion from the terranean surface into the subterranean zone to the particular depth.

In an aspect combinable with any one of the previous aspects, the aboveground sub-assembly further includes a power source.

In an aspect combinable with any one of the previous aspects, the power source includes at least one of a battery or a renewable power source.

In an aspect combinable with any one of the previous aspects, the renewable power source includes a solar power source.

In an aspect combinable with any one of the previous aspects, the power source is electrically coupled to the one or more sensors.

In an aspect combinable with any one of the previous aspects, the power source is electrically coupled to the controller.

In an aspect combinable with any one of the previous aspects, the aboveground sub-assembly further includes a wireless transmitter communicably coupled to the controller.

In an aspect combinable with any one of the previous aspects, the wireless transmitter includes at least one of a Wi-Fi transmitter, a cellular transmitter, or a satellite transmitter.

In an aspect combinable with any one of the previous aspects, the aboveground sub-assembly further includes a housing that at least partially encloses the controller.

In an aspect combinable with any one of the previous aspects, the housing includes a weatherproof housing.

An aspect combinable with any one of the previous aspects further includes at least one communication cable that communicably couples the one or more sensors and the controller.

In an aspect combinable with any one of the previous aspects, the at least one communication cable includes at least one weatherproof communication cable.

In another example implementation, a method for detecting at least one attribute associated with $CO_2$ sequestration below a terranean surface includes installing a $CO_2$ sequestration sensor system. The installing includes installing an underground sub-assembly of the $CO_2$ sequestration sensor system below a terranean surface. The underground sub-assembly includes one or more sensors configured to detect at least one attribute associated with $CO_2$ sequestration below the terranean surface. The installing also includes installing an above-ground sub-assembly of the $CO_2$ sequestration sensor system on the terranean surface proximate the underground sub-assembly. The above-ground sub-assembly includes at least one controller communicably coupled to the one or more sensors. The method further includes operating the $CO_2$ sequestration sensor system to detect at least one attribute associated with $CO_2$ sequestration below the terranean surface with at least one sensor of the one or more sensors of the installed underground sub-assembly.

An aspect combinable with the example implementation further includes detecting, with the at least one sensor, at least one of a $CO_2$ plume from below the terranean surface, a fracture generated by a $CO_2$ sequestration operation, or a change to a seismic condition below the terranean surface generated by the $CO_2$ sequestration operation.

In an aspect combinable with any one of the previous aspects, the one or more sensors include at least one of an accelerometer, a geophone, a $CO_2$ sensor, a DAS, an electromagnetic sensor, or a gravitometer.

An aspect combinable with any one of the previous aspects further includes inserting a conduit having at least one open end from the terranean surface into a subterranean zone to a particular depth.

In an aspect combinable with any one of the previous aspects, the conduit includes a volume configured to at least partially enclose the one or more sensors.

In an aspect combinable with any one of the previous aspects, the particular depth is between 1-3 feet below the terranean surface.

In an aspect combinable with any one of the previous aspects, the conduit includes a hollow tube.

In an aspect combinable with any one of the previous aspects, the conduit includes a sharpened end configured to facilitate the insertion from the terranean surface into the subterranean zone to the particular depth.

In an aspect combinable with any one of the previous aspects, the installing further includes installing a power source of the aboveground sub-assembly.

An aspect combinable with any one of the previous aspects further includes providing power to at least the aboveground sub-assembly with the power source that includes at least one of a battery or a renewable power source.

An aspect combinable with any one of the previous aspects further includes providing power to at least the aboveground sub-assembly with the renewable power source that includes a solar power source.

In an aspect combinable with any one of the previous aspects, the installing further includes electrically coupling the power source to the one or more sensors.

In an aspect combinable with any one of the previous aspects, the installing further includes electrically coupling the power source to the controller.

In an aspect combinable with any one of the previous aspects, the installing further includes connecting a wireless transmitter communicably to the controller.

In an aspect combinable with any one of the previous aspects, the wireless transmitter includes at least one of a Wi-Fi transmitter, a cellular transmitter, or a satellite transmitter.

In an aspect combinable with any one of the previous aspects, the installing further includes enclosing the controller of the aboveground sub-assembly into a housing.

In an aspect combinable with any one of the previous aspects, the housing includes a weatherproof housing.

In an aspect combinable with any one of the previous aspects, the installing further includes connecting the one or more sensors to the controller with at least one communication cable.

In an aspect combinable with any one of the previous aspects, the at least one communication cable includes at least one weatherproof communication cable.

In another example implementation, a sensor system includes an underground sub-assembly including one or more sensors configured to detect at least one attribute associated with a subterranean zone below a terranean surface; and an above-ground sub-assembly positionable on the terranean surface proximate the underground sub-assembly and including at least one controller communicably coupled to the one or more sensors.

For example, one or more sensors can be configured to detect at least one attribute associated with geothermal energy in a subterranean zone below a terranean surface. The controller can determine, for example, natural and/or hydraulic fracture sizing, directionality, and/or optimization based on the attribute of the geothermal energy detected by the one or more sensors.

As another example, one or more sensors can be configured to detect at least one attribute associated with subsurface storage of a fluid (e.g., compressed air, hydrogen, other gas storage) in a subterranean zone below a terranean surface. The controller can determine, for example, identification, characterization and monitoring of such fluid storage based on the attribute of the fluid storage detected by the one or more sensors.

As another example, one or more sensors can be configured to detect at least one attribute associated with subsurface water in a subterranean zone below a terranean surface. The controller can determine, for example, identification, characterization, imaging, hydrogeology and location of such subsurface water based on the attribute of the detected by the one or more sensors.

As another example, one or more sensors can be configured to detect at least one attribute associated with subsurface mineral resources in a subterranean zone below a terranean surface. The controller can determine, for example, identification, characterization, location, and monitoring of such subsurface minerals based on the attribute detected by the one or more sensors.

As another example, one or more sensors can be configured to detect at least one attribute associated with gas leakage (e.g., methane, hydrogen) from a subterranean zone below a terranean surface. The controller can determine, for example, identification, characterization and monitoring of such gas leakage based on the attribute detected by the one or more sensors.

Implementations of systems and methods according to the present disclosure can include one, some, or all of the following features. For example, sensor systems and methods according to the present disclosure can provide for cost and time efficient gathering of data that, for example, can signal an adverse even associated with $CO_2$ sequestration or other fluid sequestration or injection into a subterranean formation. As another example, sensor systems and methods according to the present disclosure can provide sensed data within a relatively shallow borehole, e.g., a borehole that does not require formation by a drilling or completion rig.

The details of one or more implementations of the subject matter described in this disclosure are set forth in the accompanying drawings and the description below. Other features, aspects, and advantages of the subject matter will become apparent from the description, the drawings, and the claims.

DETAILED DESCRIPTION

Figure 1:
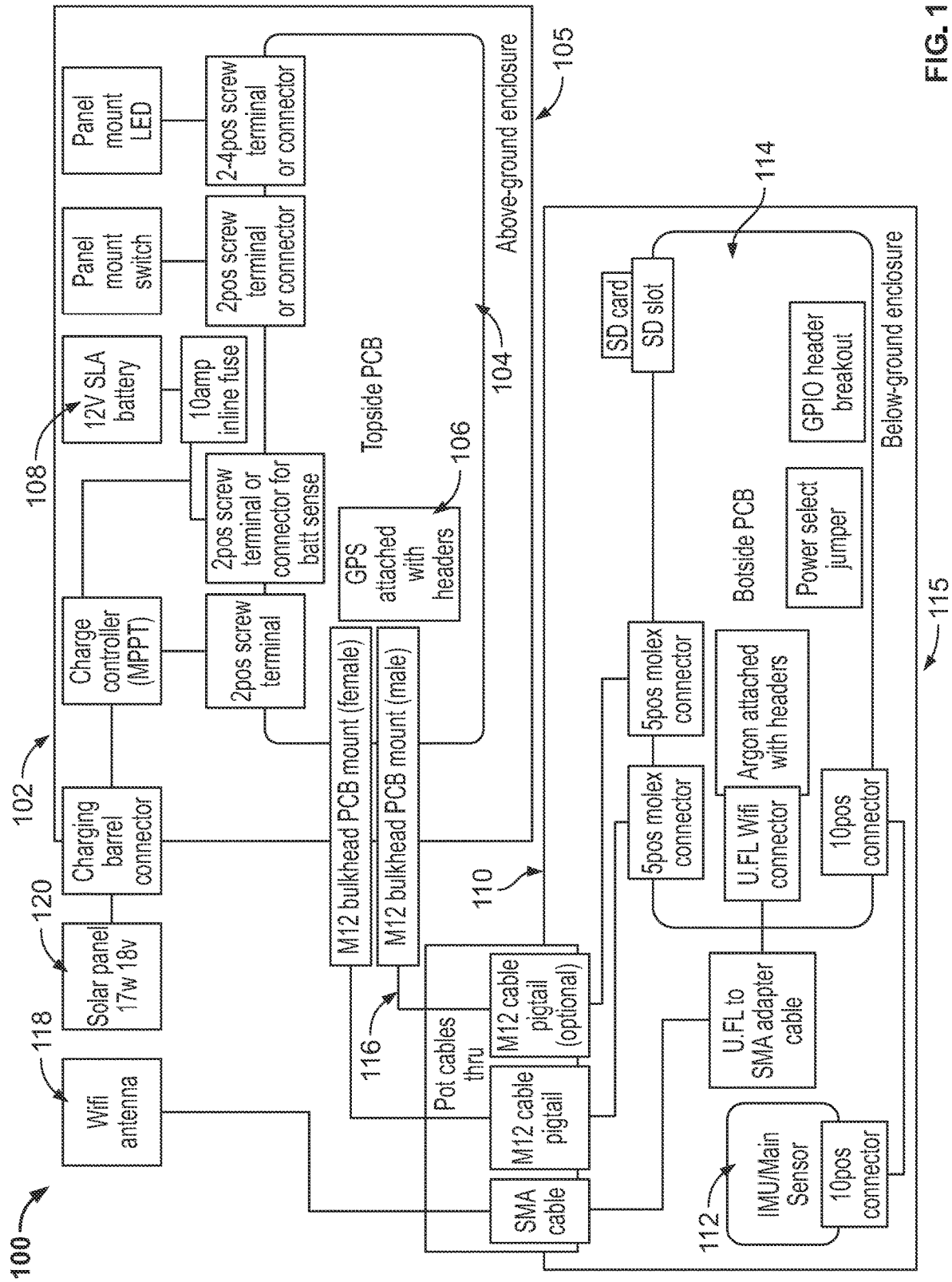
FIG. 1 depicts an example implementation of a sensor system for detecting at least one attribute associated with a subterranean zone operation, such as $CO_2$ sequestration, according to the present disclosure.

FIG. 1 depicts an example implementation of a sensor system 100 for detecting at least one attribute associated with a subterranean zone operation, such as $CO_2$ sequestration, according to the present disclosure. As shown in this example implementation, the sensor system 100 includes an aboveground sub-assembly 102 that includes a housing 105 (such as a weatherproof housing) to at least partially enclose one or more components of the sensor system 100. In some aspects, the aboveground sub-assembly 102 is configured or built to be positioned on a terranean surface (e.g., on bare ground or otherwise) and exposed to an ambient environment. As further shown in this example, the sensor system 100 includes am underground sub-assembly 110 that includes a conduit 115 suitable for enclosing one or more components of the sensor system 100 underneath the terranean surface (e.g., in contact with a subterranean zone a particular depth below the surface). Although various components of the sensor system 100 in this figures are shown either as singular components or multiple components, each component can be singular or multiple even if different than shown in this example implementation.

The aboveground sub-assembly 102, in this example implementation, includes a controller (e.g., topside PCB) 104 that is communicably coupled to one or more components of the underground sub-assembly 110 through one or more communication cables 116 (two shown in this example). Generally, the controller 104 can receive sensed or measured data from the underground sub-assembly 110 that is related, e.g., to parameters or attributes associated with the underground sequestration of $CO_2$ (e.g., through injection wellbores). In some aspects, the controller 104 can process the received data to provide conclusions or interpretations from the data.

As further shown in this example, the aboveground sub-assembly 105 includes a power source 108; in this example, a battery such as a 12V SLA battery. The power source 108 is electrically coupled to the controller 104 to provide operational power to the controller 104 (and other components as described herein). In this example, a renewable energy source 120 is also included and electrically coupled to the power source 108 to provide renewable power to the power source 108. In this example, the renewable energy source 120 is comprised of one or more solar panels; other renewable sources could include hydroelectric sources, wind energy sources, geothermal sources, or otherwise.

In this example implementation, the underground sub-assembly 110 is at least partially enclosed by the conduit 115 and includes one or more sensors 112 configured to detect or measure an attribute or parameter associated with $CO_2$ sequestration. The conduit 115, in some aspects, can be a hollow tube with a top, open end through which the one or more sensors 112 (and other components) can be inserted and enclosed (e.g., by a seal or cap). In this example, the communication cables 116 can be inserted through an open end of the conduit 115 (which is then sealed) and connect to, e.g., a controller 114 (i.e., BotSide PCB). A bottom, closed end of the conduit 115 can be, in some aspects, pointed (e.g., like a ground stake) to facilitate insertion into the subterranean zone from the surface.

The one or more sensors 112 can include one or more of a variety of different sensors. Such sensors include, for example, seismic (e.g., passive that do not require vibroseis equipment), accelerometers (singularly or in an array), gravitometers, electromagnetic sensors, distributed acoustic sensors (DAS), geophones, $CO_2$ sensors (soil or otherwise), pressure sensors, temperature sensors, or any other sensor type that can detect or measure an attribute or parameter associated with $CO_2$ sequestration. Such attributes include, for instance, $CO_2$ plumes in the subterranean zone, seismic activity associated with injected $CO_2$ sequestration, fractures or microfractures within a subterranean zone due to injected $CO_2$ sequestration, and other attributes.

As shown in this example, the one or more sensors 112 are communicably coupled to the controller 114, which can transmit sensed or measured data through the communication cables 116 to the controller 104. However, in alternate aspects, the one or more sensors 112 can be communicably coupled to the controller 104 through the communication cables 116 (i.e., in the absence of a controller 114 in the underground sub-assembly 110). Although not shown, other sensors (e.g., temperature, pressure, weather, $CO_2$, or otherwise) can also be included with the aboveground sub-assembly 102 to sense data from the terranean surface.

This example of the sensor system 100 also includes a wireless communication assembly 118. Here, the wireless communication assembly 118 is in the form of a Wi-Fi antenna; in alternative aspects, the assembly 118 can be (or also include) a cellular transmitter or a satellite transmitter. In some aspects, the sensed data from the one or more sensors 112 can be wirelessly transmitted through the wireless communication assembly 118 to a remote location, e.g., for further analysis. In some aspects, sensed data that has been pre-processed by the controller 104 can be wirelessly transmitted through the wireless communication assembly 118 to a remote location, e.g., for further analysis. Although illustrated as communicably coupled to the underground sub-assembly 110 (and controller 114), the wireless communication assembly 118 can be communicably coupled to the controller 104 (additionally or alternatively).

In this example implementation, the sensor system 100 comprises a portable and highly mobile and repeatable package for measuring data associated with $CO_2$ sequestration. In some aspects, such a sensor system 100 can be used for other tasks related to seismic or geological study or survey. For example, classical data acquisition for the purposes of geological and geophysical modeling is extremely expensive. Also, the existing data acquisition methods lead towards model bias and often do not offer the data fidelity needed to solve large detailed models. For example, current seismic data sets are band limited and lead to aliasing the data via frequency notches that could be filled by logging additional data in the low frequency (<5 Hz) and high frequency (>85 Hz). Although the range of seismic data (>5 Hz and <85 Hz) is very effective for targeting porous reservoirs, their abundance biases those features in machine learning models, leading to a lack of data of other features, such as deep discontinuities or shallow geology. These other features can be important, e.g., for building a differentiated global subsurface model.

In most cases, data acquisition is set up to identify particular targets, and thus in any one location data with respect to the frequency domain is quite sparse, while it can still be quite densely sampled in space. The acquisition of data, in some aspects, should be usable in a meaningful machine learning framework without the need for heavy data processing and conditioning. In some aspects, the sensor system 100 represents a package designed and deployed as a multi-scale, high-resolution data acquisition hardware and software package that can be permanent, but can also be redeployed to other locations when necessary. In some aspects, multiple (100s, 1000s, 10,000s) of sensor systems 100 can be deployed to acquire the correct data to build a "global subsurface model" which would yield advancements in many applications, including: earthquake hazard prediction; mineral type identification; water/brine bearing reservoirs identification; Rare Earth Mineral (REM) and other mineral target location and abundance prediction;

surficial and subsurface geology maps for hydrologic process modeling; geothermal energy site identification and monitoring, as well as $CO_2$ sequestration enhancement. In some aspects, the sensor systems 100 can include (or be integrated with) a processing software suite, which will take native logged data and transform it into standard format, as well as pre-process the data for machine learning models.

The sensor system 100, therefore, can represent an acquisition package that can aid and enhance current data acquisition methodologies used in industry and research data collected by academia or governmental agencies/organizations. Focusing on adding value to the current global subsurface model and filling the described gaps can augment existing data.

In some aspects, the sensor system 100 may achieve the following performance: 5 meter model resolution scale for global block model; vertical and horizontal resolution; full 3D multi-azimuthal data coverage; logging extensible to 1 meter resolution, and multi-scale physics sensors for blending models effectively.

As described, the underground sub-assembly 110 includes one or more sensors 112. In some aspects, the sensors 112 can augment existing data taken by conventional sensor packages, including: seismic data, wireline logs, core data, technical reports, satellite/remote sensing data, hyperspectral images, teleseismic wavefield data, electromagnetic, gravity, and/or fiber arrays. The sensors 112 can also include: STS-1 like stations, MagnetoTelluric, wireline and core logging, Fiber array for RT logging, and/or ground penetrating radar In some aspects, the sensor system 100 has frequency sensitivity from 0.01 Hz to over 300 Hz data, while minimizing frequency notched that could alias the data for machine learning usage. While most of the above hardware sensors are conventionally used, most of them are not being used for $CO_2$ sequestration or sub-earth modeling or as a package.

In some aspects, the sensor system 100 can provide scalable data acquisition and analysis. For example, the sensor system 100 can allow for very high frequency "local" data to be collected, as well as broadband crustal data to help build the best subsurface "container" and broaden resolution scales. Data from initial deployments of sensor systems 100 can allow for further understanding of spatial deployment to achieve good subsurface coverage over a target area. In some aspects, the sensor system 100 can provide for full frequency range coverage to allow true geologic feature mapping. The sensor system 100 can provide a flat frequency spectrum over a very broad range, this could lead to better geologic models.

Figure 2:
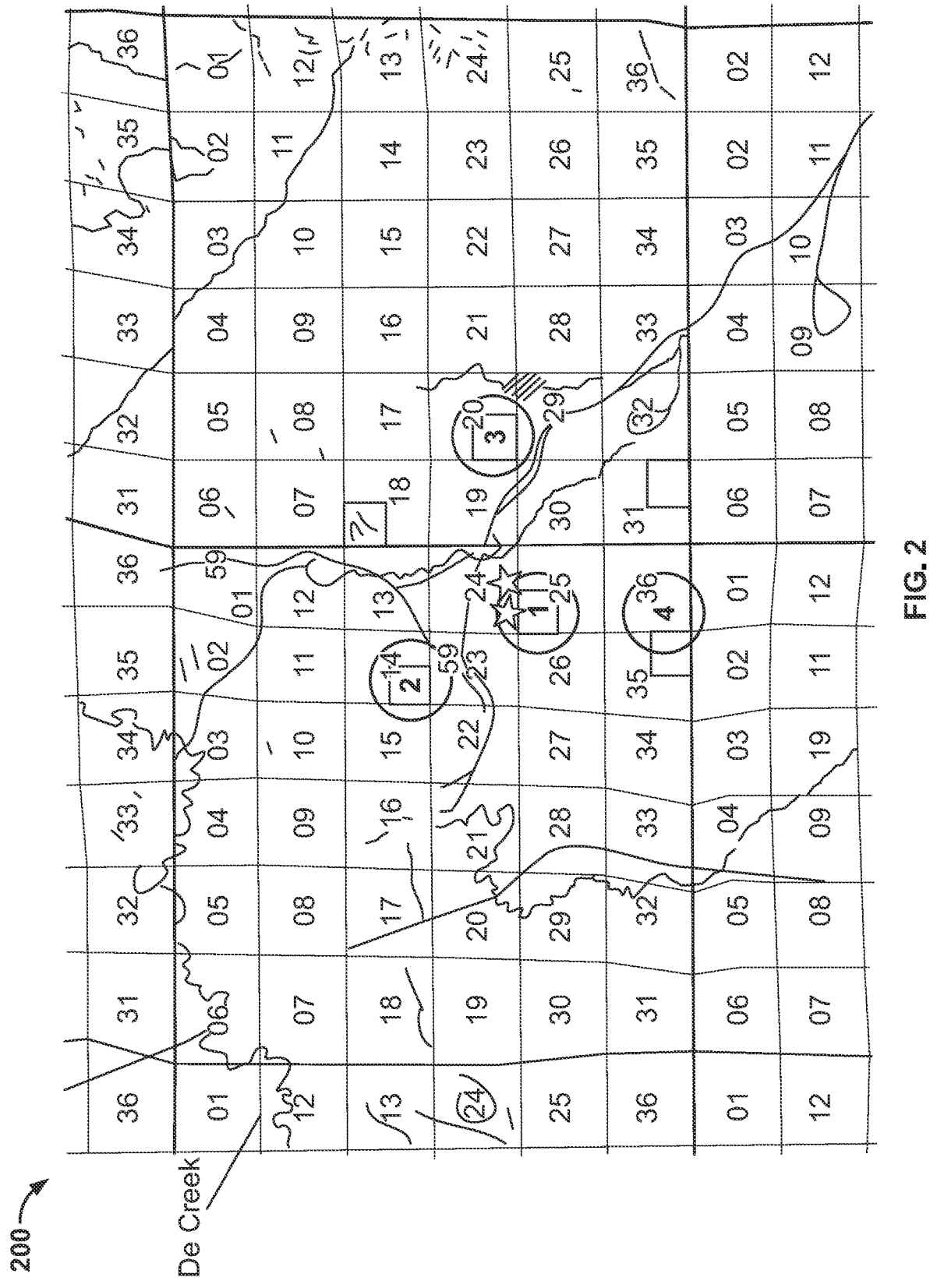
FIG. 2 is a plot of one or more placement locations for the sensor system of FIG. 1 proximate a $CO_2$ sequestration site according to the present disclosure.

FIG. 2 is a plot 200 of one or more placement locations for the sensor system 100 of FIG. 1 proximate a $CO_2$ sequestration site according to the present disclosure. As shown on the plot 200, $CO_2$ sequestration (i.e., a $CO_2$ injection well) can occur at site "1" (circled). In some aspects, multiple sensor systems 100 can be placed proximate site 1, with the underground sub-assembly 110 of each system 100 inserted, e.g., 1-3 feet underground and the aboveground sub-assembly 102 of each system 100 residing on the surface proximate the installed underground sub-assembly 110 (and connected by communication cable 116). In some aspects, sensor systems 100 can also be installed at locations labeled "2," "3," and "4" to provide triangulated data based on the activity occurring at site 1. In this example, 24 sensor systems 100 across the four sites can be installed and aligned with the conventional deployments of geophones. The sensor systems 100, in this example, can be arranged in a cross-shaped array spaced within a 50 meter diameter circle (shown on the plot 200). During operation of the sensor systems 100, the following actions can occur: gather data from the sensors 112, compare this data with data gathered by conventional geophones, and use the gathered data to fine tune system 100 deployment design (e.g., in the future or at different sites).

In some aspects, a wireless communication assembly 118 for each of the deployed sensor systems 100 can be part of a mesh network that, e.g., transmits data to a central node (e.g., a central control system). In some aspects, data can be aggregated at the central node, pre-processed or analyzed, and/or transmitted (or otherwise exposed) in bulk to another remote location for analysis.

Figure 3:
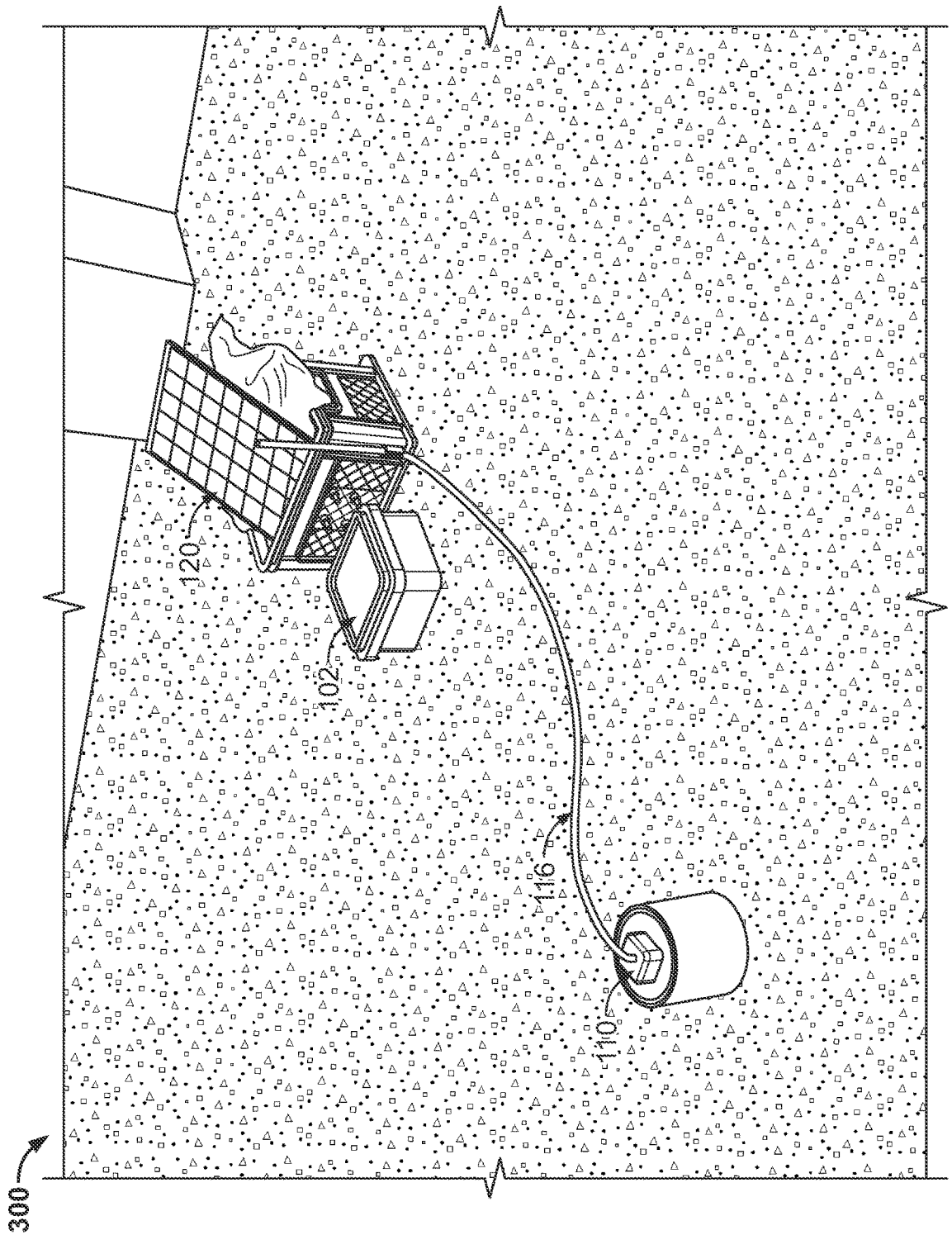
FIG. 3 is an image of an example implementation of an installed sensor system for detecting at least one attribute associated with $CO_2$ sequestration according to the present disclosure.

FIG. 3 is an image 300 of an example implementation of an installed sensor system 100 for detecting at least one attribute associated with $CO_2$ sequestration according to the present disclosure. The installed sensor system 100 can represent, for example, a system installed near one or more of the sites 1-4 shown in plot 200. As shown, several components of the sensor system 100 are labeled, including the underground sub-assembly 110 (shown partially installed), the communication cable(s) 116, the aboveground sub-assembly 102, and the renewable power source 120 (as a PV solar panel). In this example, the installed sensor system 100 includes a PVC weather-resistant box (housing 105), with approximate dimensions of 9.0×9.0×5.7 inches. The weather-resistant box contains electronics (e.g., controller 104 and other components) as well as a lead-acid battery (power source 108). Also included is a sealed tube (e.g., conduit 115), approximately 4 inches in diameter and 11 inches in length) that contains the sensor (sensor 112) that will be buried 1-3 ft. underground and is connected to the box (by cables 116). In some aspects, weight can be added to or on top of the aboveground box to secure the position. The box can also have the solar panel attached to it for recharging and flagpole for visibility.

Figure 4:
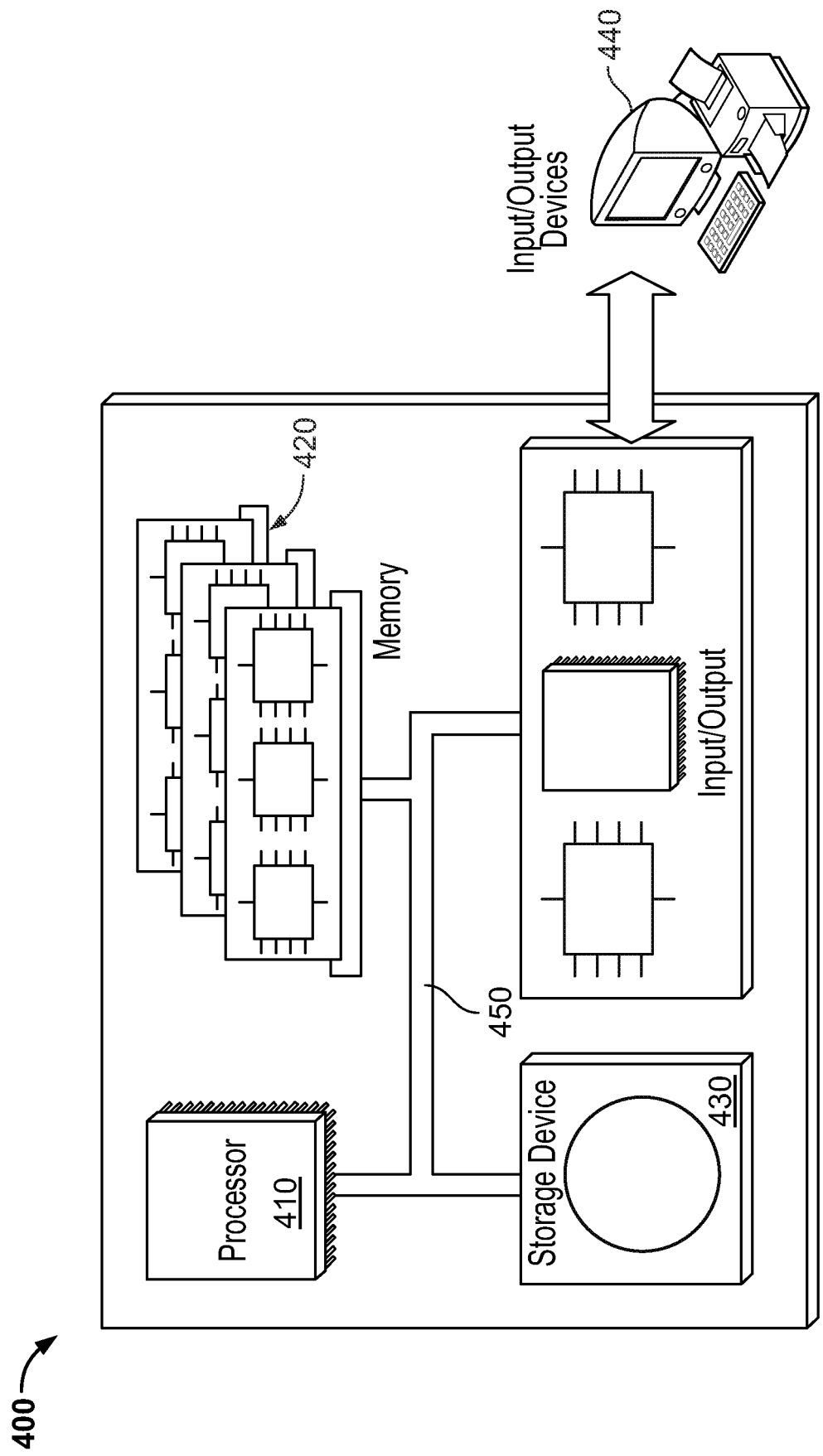
FIG. 4 depicts a control system for a sensor system for detecting at least one attribute associated with $CO_2$ sequestration according to the present disclosure.

FIG. 4 is a schematic diagram of a control system 400. The system 400 can be used to carry out the operations described in association with any of the computer-implemented methods described previously, according to some implementations and/or, for example, as all or part of each of the controllers 104 and 114. In some implementations, computing systems and devices and the functional operations described in this specification can be implemented in digital electronic circuitry, in tangibly-embodied computer software or firmware, in computer hardware, including the structures disclosed in this specification and their structural equivalents, or in combinations of one or more of them. The system 400 is intended to include various forms of digital computers, such as laptops, desktops, workstations, servers, blade servers, mainframes, and other appropriate computers. The system 400 can also include mobile devices, such as personal digital assistants, cellular telephones, smartphones, and other similar computing devices. Additionally, the system can include portable storage media, such as Universal Serial Bus (USB) flash drives. For example, the USB flash drives may store operating systems and other applications. The USB flash drives can include input/output components, such as a wireless transducer or USB connector that may be inserted into a USB port of another computing device.

The system 400 includes a processor 410, a memory 420, a storage device 430, and an input/output device 440. Each of the components 410, 420, 430, and 440 are interconnected using a system bus 450. The processor 410 is capable of processing instructions for execution within the system 400. The processor may be designed using any of a number of architectures. For example, the processor 410 may be a CISC (Complex Instruction Set Computers) processor, a RISC (Reduced Instruction Set Computer) processor, or a MISC (Minimal Instruction Set Computer) processor.

In one implementation, the processor 410 is a single-threaded processor. In another implementation, the processor 410 is a multi-threaded processor. The processor 410 is capable of processing instructions stored in the memory 420 or on the storage device 430 to display graphical information for a user interface on the input/output device 440.

The memory 420 stores information within the system 400. In one implementation, the memory 420 is a computer-readable medium. In one implementation, the memory 420 is a volatile memory unit. In another implementation, the memory 420 is a non-volatile memory unit.

The storage device 430 is capable of providing mass storage for the system 400. In one implementation, the storage device 430 is a computer-readable medium. In various different implementations, the storage device 430 may be a floppy disk device, a hard disk device, an optical disk device, or a tape device.

The input/output device 440 provides input/output operations for the system 400. In one implementation, the input/output device 440 includes a keyboard and/or pointing device. In another implementation, the input/output device 440 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, e.g., in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system, including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits). The machine learning model can run on Graphic Processing Units (GPUs) or custom machine learning inference accelerator hardware.

To provide for interaction with a user, the features can be implemented on a computer having a display device such as a CRT (cathode ray tube) or LCD (liquid crystal display) monitor for displaying information to the user and a keyboard and a pointing device, such as a mouse or a trackball by which the user can provide input to the computer. Additionally, such activities can be implemented via touchscreen flat-panel displays and other appropriate mechanisms.

The features can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

The computer system can include clients and servers. A client and server are generally remote from each other and typically interact through a network, such as the described one. The relationship of client and server arises by virtue of computer programs running on the respective computers and having a client-server relationship to each other.

While this specification contains many specific implementation details, these should not be construed as limitations on the scope of any implementations or of what may be claimed, but rather as descriptions of features specific to particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A $CO_2$ sequestration sensor system, comprising:
an underground sub-assembly comprising one or more sensors configured to detect at least one attribute associated with $CO_2$ sequestration below a terranean surface, the one or more sensors comprising a frequency sensitivity of between 0.01 Hz and 300 Hz, the underground sub-assembly comprising:
a conduit having at least one open end configured for insertion from the terranean surface into a subterranean zone to a particular depth, the conduit comprising a volume that is humanly accessible from the terranean surface through the at least one open end and sized to at least partially enclose the one or more sensors, and
a cap or seal configured to fit over the at least one open end to enclose the one or more sensors within the volume; and
an above-ground sub-assembly positionable on the terranean surface proximate the underground sub-assembly and comprising at least one controller communicably coupled to the one or more sensors and a housing that at least partially encloses the controller and is less than a cubic foot in volume.

2. The system of claim 1, wherein the at least one attribute comprises at least one of a $CO_2$ plume from below the terranean surface, a fracture generated by a $CO_2$ sequestration operation, or a change to a seismic condition below the terranean surface generated by the $CO_2$ sequestration operation.

3. The system of claim 1, wherein the one or more sensors comprises at least one of an accelerometer, a geophone, a $CO_2$ sensor, a DAS, an electromagnetic sensor, or a gravitometer.

4. The system of claim 1, wherein the particular depth is between 1-3 feet below the terranean surface.

5. The system of claim 1, wherein the conduit comprises a hollow tube.

6. The system of claim 1, wherein the conduit comprises a sharpened end opposite the at least one open end and configured to facilitate the insertion from the terranean surface into the subterranean zone to the particular depth.

7. The system of claim 1, wherein the aboveground sub-assembly further comprises a power source.

8. The system of claim 7, wherein the power source comprises at least one of a battery or a renewable power source.

9. The system of claim 8, wherein the renewable power source comprises a solar power source.

10. The system of claim 7, wherein the power source is electrically coupled to the one or more sensors.

11. The system of claim 7, wherein the power source is electrically coupled to the controller.

12. The system of claim 1, wherein the aboveground sub-assembly further comprises a wireless transmitter communicably coupled to the controller.

13. The system of claim 12, wherein the wireless transmitter comprises at least one of a Wi-Fi transmitter, a cellular transmitter, or a satellite transmitter.

14. The system of claim 1, wherein the housing comprises a weatherproof housing.

15. The system of claim 1, further comprising at least one communication cable that communicably couples the one or more sensors and the controller.

16. The system of claim 15, wherein the at least one communication cable comprises at least one weatherproof communication cable.

17. A method for detecting at least one attribute associated with $CO_2$ sequestration below a terranean surface, comprising:
installing a $CO_2$ sequestration sensor system, the installing comprising:
installing an underground sub-assembly of the $CO_2$ sequestration sensor system below a terranean surface, the underground sub-assembly comprising:
one or more sensors configured to detect at least one attribute associated with $CO_2$ sequestration below the terranean surface, the one or more sensors comprising a frequency sensitivity of between 0.01 Hz and 300 Hz,
a conduit having at least one open end configured for insertion from the terranean surface into a subterranean zone to a particular depth, the conduit comprising a volume that is humanly accessible from the terranean surface through the at least one open end and sized to at least partially enclose the one or more sensors, and
a cap or seal configured to fit over the at least one open end to enclose the one or more sensors within the volume, and
installing an above-ground sub-assembly of the $CO_2$ sequestration sensor system on the terranean surface proximate the underground sub-assembly, the above-ground sub-assembly comprising at least one controller communicably coupled to the one or more sensors and a housing that at least partially encloses the controller and is less than a cubic foot in volume; and
operating the $CO_2$ sequestration sensor system to detect at least one attribute associated with $CO_2$ sequestration below the terranean surface with at least one sensor of the one or more sensors of the installed underground sub-assembly.

18. The method of claim 17, further comprising detecting, with the at least one sensor, at least one of a $CO_2$ plume from below the terranean surface, a fracture generated by a $CO_2$ sequestration operation, or a change to a seismic condition below the terranean surface generated by the $CO_2$ sequestration operation.

19. The method of claim 17, wherein the one or more sensors comprise at least one of an accelerometer, a geophone, a $CO_2$ sensor, a DAS, an electromagnetic sensor, or a gravitometer.

20. The method of claim 17, wherein the particular depth is between 1-3 feet below the terranean surface.

21. The method of claim 17, wherein the conduit comprises a hollow tube.

22. The method of claim 17, wherein the conduit comprises a sharpened end opposite the at least one open end and configured to facilitate the insertion from the terranean surface into the subterranean zone to the particular depth.

23. The method of claim 17, wherein the installing further comprises installing a power source of the aboveground sub-assembly.

24. The method of claim 23, further comprising providing power to at least the aboveground sub-assembly with the power source that comprises at least one of a battery or a renewable power source.

25. The method of claim 24, further comprising providing power to at least the aboveground sub-assembly with the renewable power source that comprises a solar power source.

26. The method of claim 23, wherein the installing further comprises electrically coupling the power source to the one or more sensors.

27. The method of claim 23, wherein the installing further comprises electrically coupling the power source to the controller.

28. The method of claim 17, wherein the installing further comprises connecting a wireless transmitter communicably to the controller.

29. The method of claim 28, wherein the wireless transmitter comprises at least one of a Wi-Fi transmitter, a cellular transmitter, or a satellite transmitter.

30. The method of claim 17, wherein the housing comprises a weatherproof housing.

31. The method of claim 17, wherein the installing further comprises connecting the one or more sensors to the controller with at least one communication cable.

32. The method of claim 31, wherein the at least one communication cable comprises at least one weatherproof communication cable.

* * * * *